United States Patent
Vanderploeg et al.

(10) Patent No.: US 10,300,172 B2
(45) Date of Patent: May 28, 2019

(54) MATRIX FOR ENHANCED DELIVERY OF OSTEOINDUCTIVE MOLECULES IN BONE REPAIR

(71) Applicant: Bioventus LLC., Durham, NC (US)

(72) Inventors: Eric Vanderploeg, Stoneham, MA (US); Howard Seeherman, Cambridge, MA (US); Christopher G. Wilson, Auburndale, MA (US); John Wozney, Hudson, MA (US); Christopher Todd Brown, Chelmsford, MA (US)

(73) Assignee: Bioventus, LLC., Durham, NC (US)

( * ) Notice: Subject to any disclaimer, the term of this patent is extended or adjusted under 35 U.S.C. 154(b) by 26 days.

(21) Appl. No.: 15/339,834

(22) Filed: Oct. 31, 2016

(65) Prior Publication Data

US 2017/0209623 A1    Jul. 27, 2017

Related U.S. Application Data

(60) Provisional application No. 62/248,861, filed on Oct. 30, 2015.

(51) Int. Cl.
| | |
|---|---|
| *A61L 27/56* | (2006.01) |
| *A61L 27/46* | (2006.01) |
| *A61L 27/54* | (2006.01) |
| *A61L 24/00* | (2006.01) |
| *A61L 27/10* | (2006.01) |
| *A61L 27/24* | (2006.01) |

(52) U.S. Cl.
CPC ........... *A61L 27/56* (2013.01); *A61L 24/0015* (2013.01); *A61L 24/0036* (2013.01); *A61L 24/0073* (2013.01); *A61L 27/10* (2013.01); *A61L 27/24* (2013.01); *A61L 27/46* (2013.01); *A61L 27/54* (2013.01); *A61L 2300/252* (2013.01); *A61L 2300/414* (2013.01); *A61L 2430/02* (2013.01)

(58) Field of Classification Search
CPC .......... A61L 2300/252; A61L 2430/02; A61L 24/0073; A61L 27/10; A61L 27/24; A61L 27/54; A61L 27/56
See application file for complete search history.

(56) References Cited

U.S. PATENT DOCUMENTS

| | | | |
|---|---|---|---|
| 4,394,370 A | 7/1983 | Jefferies | |
| 5,385,887 A | 1/1995 | Yim | |
| 7,722,895 B1 * | 5/2010 | McKay | ............... A61B 17/707 106/160.1 |
| 8,048,857 B2 * | 11/2011 | McKay | ............ A61B 17/00491 424/422 |
| 9,757,494 B2 | 9/2017 | Amedee et al. | |
| 2005/0119761 A1 | 6/2005 | Matsumoto | |
| 2009/0169532 A1 | 7/2009 | Ying et al. | |
| 2009/0305983 A1 | 12/2009 | Ying et al. | |
| 2010/0248368 A1 * | 9/2010 | Lynn | ....................... A61L 27/46 435/404 |
| 2012/0219599 A1 | 8/2012 | Hans Moore | |
| 2013/0028717 A1 | 1/2013 | Helvaci et al. | |
| 2013/0224277 A1 | 8/2013 | Amedee et al. | |
| 2014/0308332 A1 | 10/2014 | Lynch et al. | |
| 2015/0328365 A1 | 11/2015 | Amedee et al. | |
| 2017/0319741 A1 | 11/2017 | Amedee et al. | |

FOREIGN PATENT DOCUMENTS

| | | | | |
|---|---|---|---|---|
| EP | 1344538 A1 | 9/2003 | | |
| JP | 2009528080 A | 8/2009 | | |
| JP | 2013540465 A | 11/2013 | | |
| JP | 2013545584 A | 12/2013 | | |
| WO | 9507108 A2 | 3/1995 | | |
| WO | 9807108 A1 | 2/1998 | | |
| WO | 2006082442 A1 | 8/2006 | | |
| WO | WO-2006082442 A1 * | 8/2006 | ......... A61L 24/0036 |
| WO | 2013152418 A1 | 10/2013 | | |

OTHER PUBLICATIONS

International Search Report and Written Opinion; PCT/US2016/059782 dated Feb. 3, 2017, 9 pages.
International Search Report & Written Opinion; Appln No. PCT/US2015/067891; dated Mar. 16, 2016.

* cited by examiner

*Primary Examiner* — Andrew S Rosenthal

(57) ABSTRACT

Systems and methods for preparing osteoinductive synthetic bone grafts are provided in which a porous ceramic granule, which may be incorporated within a biocompatible matrix material, is loaded with an osteoinductive agent. Loading of granules is facilitated in some cases by the use of low-pH buffers and pre-treatments.

19 Claims, 10 Drawing Sheets

 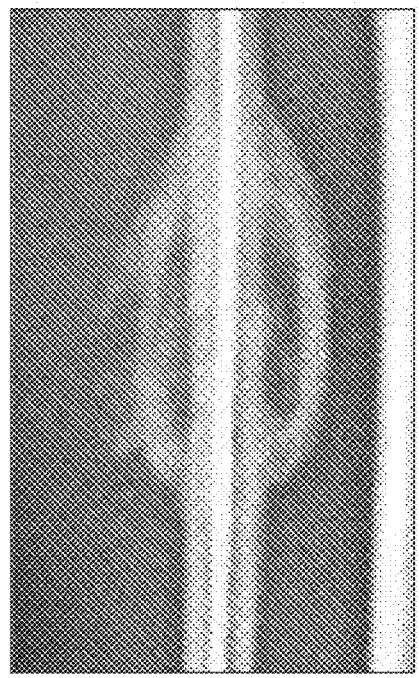
FIG. 1A  FIG. 1B
 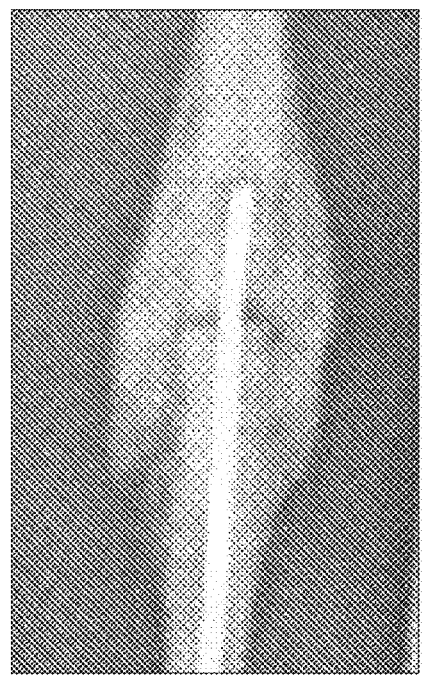
FIG. 1C  FIG. 1D

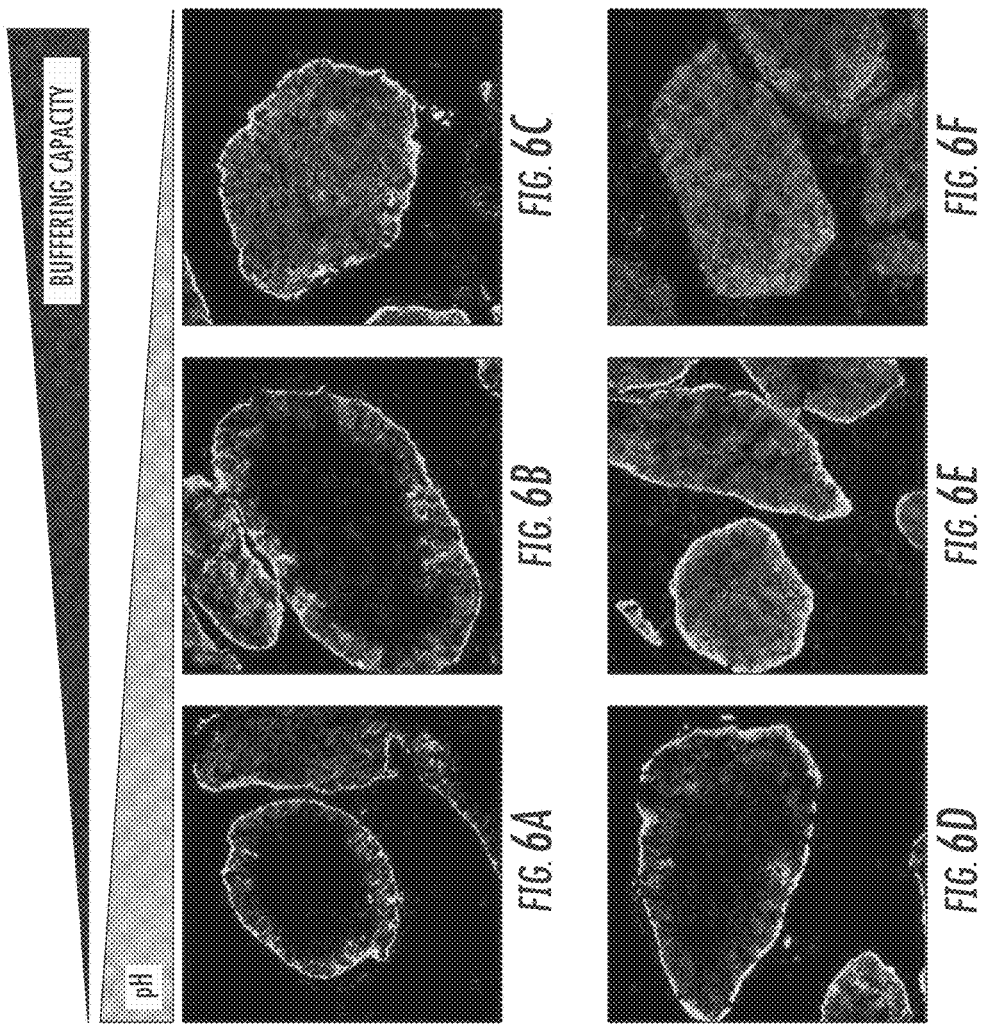

MATRIX FOR ENHANCED DELIVERY OF OSTEOINDUCTIVE MOLECULES IN BONE REPAIR

This application claims priority to and the benefit of, and incorporates herein by reference in its entirety U.S. Provisional Application Ser. No. 62/248,861, filed Oct. 30, 2015.

FIELD OF THE INVENTION

This application relates to medical devices and biologic therapies, and more particularly to bone cements, bone putties and granule-binder composites.

BACKGROUND

Bone grafts are used in roughly two million orthopedic procedures each year, and general take one of three forms. Autografts, which typically consist of bone harvested from one site in a patient to be grafted to another site in the same patient, are the benchmark for bone grafting materials, inasmuch as these materials are simultaneously osteoconductive (serving as a scaffold for new bone growth), osteoinductive (promoting the development of osteoblasts) and osteogenic (containing osteoblasts which form new bone). However, limitations on the supply of autografts have necessitated the use of cadaver-derived allografts. These materials are less ideal than autografts, however, as allografts may trigger host-graft immune responses or may transmit infectious or prion diseases, and are often sterilized or treated to remove cells, eliminating their osteogenicity.

Given the shortcomings of human-derived bone graft materials, there has been a long-standing need in the field for synthetic bone graft materials. Synthetic grafts typically comprise calcium ceramics and/or cements delivered in the form of a paste or a putty. These materials are osteoconductive, but not osteoinductive or osteogenic. To improve their efficacy, synthetic calcium-containing materials have been loaded with osteoinductive materials, particularly bone morphogenetic proteins (BMPs), such as BMP-2, BMP-7, or other growth factors such as fibroblast growth factor (FGF), insulin-like growth factor (IGF), platelet-derived growth factor (PDGF), and/or transforming growth factor beta (TGF-β). However, significant technical challenges have prevented the efficient incorporation of osteoinductive materials into synthetic bone graft substitutes which, in turn, has limited the development of high-quality osteoinductive synthetic bone graft materials.

One such challenge has been the development of a graft matrix which delivers an osteoinductive material over time, rather than in a single short burst release, and which has appropriate physical characteristics to support new bone growth. The generation of a material with appropriate physical characteristics involves, among other things, balancing the requirement that such materials be rigid enough to bear loads that will be applied to the graft during and after implantation with the requirements that they remain porous enough to allow for cell and tissue infiltration and degrade or dissolve at a rate which permits replacement of the graft by new bone, and the separate requirement that they elute the osteoinductive material in a temporal and spatial manner that is appropriate for bone generation. It is only the combination of the above design criteria that will result in an optimal graft matrix for promoting new bone formation and ultimate healing. For example, BMP-eluting synthetic bone grafts currently available commercially do not meet these requirements, and a need exists for a bone graft material which is optimized for the delivery of osteoinductive materials such as BMPs.

SUMMARY OF THE INVENTION

The present invention addresses an important unmet need in the field by providing synthetic bone graft materials with improved elution of osteoinductive proteins in combination with optimal physical characteristics, as well as methods of making and using the same. In one aspect, the present invention relates to a composition that includes a porous biocompatible matrix with a plurality of micropores with an average size in the range of 100 to 500 microns and a calcium ceramic granule (which optionally, but does not necessarily have a specific surface area greater than 30 m$^2$/g) contacting the biocompatible matrix, which granule has an interconnected network of micropores defining at least one surface on the interior of the granule. In some cases, the ceramic granule has a pH in the range of 5.5 to 6.0 (as measured in a slurry of granules and water or another neutral, non-buffering solution). Compositions of the present invention can be configured for loading with an osteoinductive protein and to retain at least 50% of such osteoinductive protein for 7 days or more after implantation into a patient. Along these lines, in some cases the composition includes an osteoinductive protein associated with that at least one surface on the interior of the granule, such that a concentration of the osteoinductive protein near the centroid of the calcium ceramic granule is similar to (e.g. not less than about 33% of) a concentration of the osteoinductive protein on the external surface of the calcium ceramic granules. For example, in some cases, the concentration of the osteoinductive protein on an interior surface near the centroid (i.e. within a radius of approximately 20% or, in some cases, 10% of the average distance from the centroid to the outer surface) can be at least 33% of the concentration of the protein found on the outer surface of the granule (e.g. a ratio of the concentration of protein on the surface to concentration near the centroid can be less than 3). The biocompatible matrix, which can be formed from collagen or a synthetic polymer, optionally includes a plurality of macropores with an average diameter in the 1-2 mm range and, optionally or additionally, is characterized by sufficient column strength to resist at least 50 kPa of pressure at 50% linear strain.

In another aspect, the invention relates to a method of treating a patient that includes a step of contacting a bony tissue of the patient with a composition that includes (a) a porous biocompatible matrix, the matrix including a plurality of macropores having an average size of about 100 μm to about 500 μm, (b) a calcium ceramic granule contacting the porous biocompatible matrix having an interconnected network of micropores defining at least one surface on an interior of the granule, and (c) an osteoinductive protein associated with the at least one surface on the interior of the granule, which osteoinductive protein is distributed on a portion of the at least one surface near the centroid of the granule and on a portion of the at least one surface near the exterior of the granule. The bony tissue is optionally a site of a traumatic injury to the bone and/or a vertebra. In some cases, the calcium ceramic granule has a pH of about 5.5 to about 6.0, and/or a concentration of the osteoinductive protein near the centroid of the calcium ceramic granule is not less than about 33% of a concentration of the osteoinductive protein on the external surface of the calcium ceramic granules. The biocompatible matrix can include collagen or a synthetic polymer in some cases. Alternatively or additionally, the method can include a step of the step of wetting the composition with a solution comprising the osteoinductive protein, thereby associating the osteoinductive protein with the at least one surface In yet another aspect, the present invention relates to a kit for treating a patient that includes a carrier and a vessel holding an osteoinductive protein in a form in which the osteoinductive protein can be added to a fluid to form a solution. The carrier includes a porous biocompatible matrix including a plurality of macropores having an average size of about 100 μm to about 500 μm and a calcium ceramic granule contacting the porous biocompatible matrix, which granules has an interconnected network of micropores defining at least one surface on an interior of the granule. The solution formed by adding fluid to the vessel holding the osteoinductive protein, meanwhile is adapted to wet the carrier, thereby associating the osteoinductive protein with the at least one surface on the interior of the granule, thereby forming an implant. In various instances, the porous biocompatible matrix additionally has a plurality of macropores with an average diameter of about 1 mm to 2 mm, and/or is formed from collagen, and/or is formed of a synthetic polymer. Alternatively or additionally, the implant formed from the components of the kit has sufficient column strength to resist at least 50 kPa of pressure at 50% linear strain.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted. It will be understood that the invention is not necessarily limited to the particular embodiments illustrated herein.

FIG. 1A-D shows a comparison of callus formation in a nonhuman primate fibula osteotomy model in response to treatment with BMP-2 delivered in an absorbable collagen sponge (ACS) compared to treatment with BMP-2 delivered in a granulating calcium phosphate matrix (CPM) at 8 weeks. The BMP-2/ACS-treated osteotomy shown in 1A and B has a hollow callus architecture resulting from bone formation outside the microporous ACS carrier rather than within the ACS carrier. In contrast the BMP-2/CPM-treated repair shown in 1C and D has a much more uniform callus architecture resulting from bone formation between the granulated macroporous carrier.

FIG. 6A-F shows micrographs of untreated (6A-C) and acid pre-treated ("etched") (6D-F) granules loaded with fluorescently labeled BMP in varying buffer compositions. In the first column (6A&D), granules were loaded with protein in a low buffering capacity pH 4.0 buffer ("1× dBMP Buffer"; for composition see Table 1). In the second column (6B&E), the granules were loaded with protein in an intermediate buffering capacity pH 3.5 buffer ("5× dBMP Buffer"). In the third column, the granules were loaded with protein in a high buffering capacity pH 3.0 buffer ("10× dBMP Buffer"). The distribution of protein shifts from being concentrated at the surface of the granules in 6A&D to a more uniform distribution as buffering capacity increases and pH decreases (i.e. the protein is distributed along pore surfaces near the centroid and near the exterior surface of the granules). The combination of etched granules and the 10× dBMP buffer gave the most uniform distribution of protein.

FIG. 7A-C demonstrates that in a weakly buffered system the vast majority of the BMP is confined near the exterior of the granules, whereas in a strongly buffered system the BMP is more uniformly distributed between both the centroid and the exterior. The ratio of peripheral to centroid fluorescence is lower (e.g. closer to 1:1) in the strong buffer with at least 30% of the total signal found in the centroid. FIG. 7D demonstrates that this is due, at least in part, to an increase in signal in the centroid of the granule.

DETAILED DESCRIPTION

Osteoinductive Compositions

Figure 2:
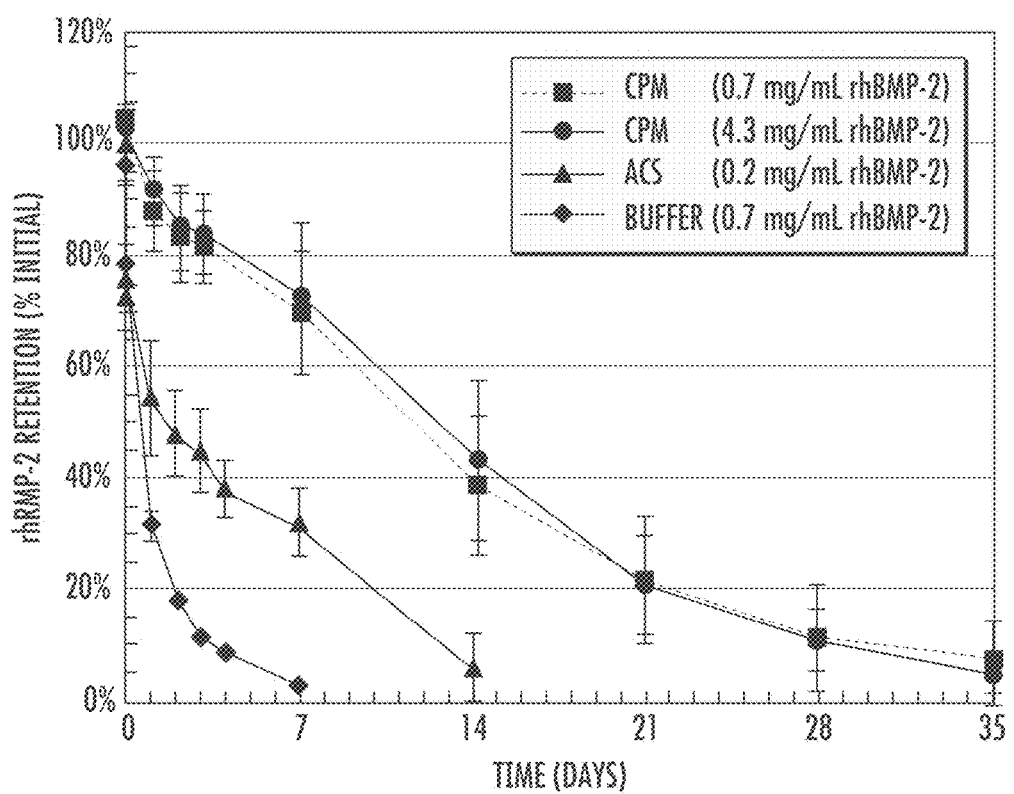
FIG. 2 shows in-situ retention of rhBMP-2 (% of initial dose, mean±SD) vs time (days) after injection with rhBMP-2/calcium phosphate matrix (CPM, 0.7 and 4.2 mg/mL) compared to 0.2 mg/mL rhBMP-2 delivered on an absorbable collagen sponge (ACS) and in buffer (0.7 mg/mL) in a rabbit ulna osteotomy model.
Figure 3:
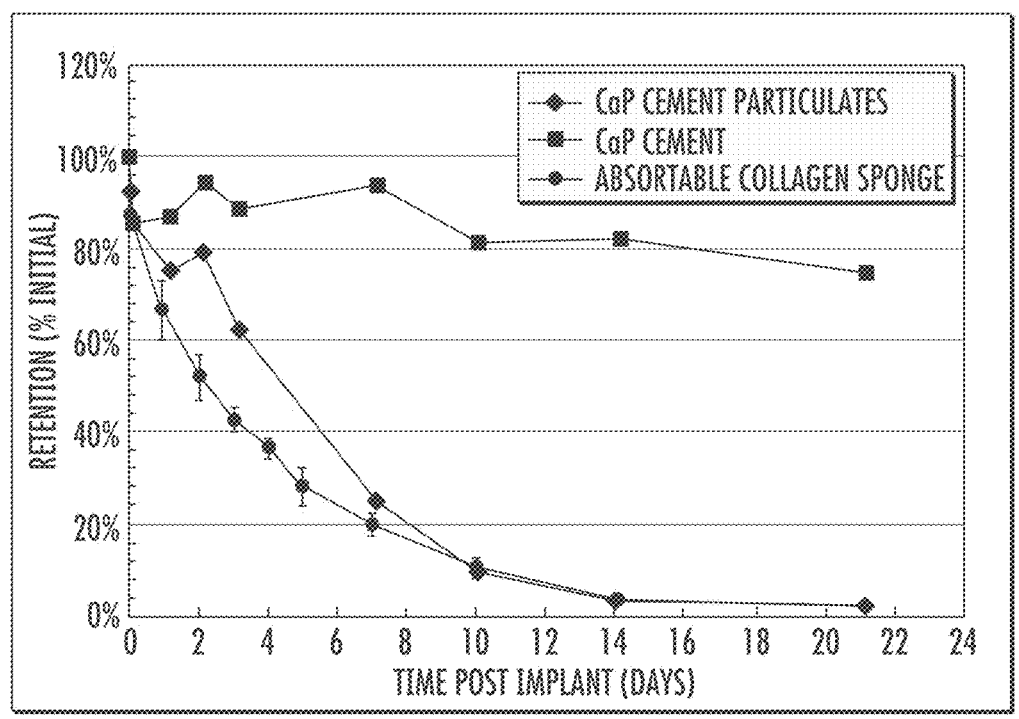
FIG. 3 shows the retention profile for BMP-2 delivered in a calcium phosphate (CaP) cement compared to BMP-2 loaded onto the surface of preformed CaP cement granules and BMP-2 delivered in an absorbable collagen sponge (ACS) in a rat intramuscular pouch model. Retention of BMP-2 contained within the CaP cement is significantly longer than retention of BMP-2 loaded onto the surface of the preformed CaP cement granules. BMP-2 retention from surface coated CaP cement granules is similar to the less than optimal retention observed when BMP-2 is delivered in ACS.
Figure 4:
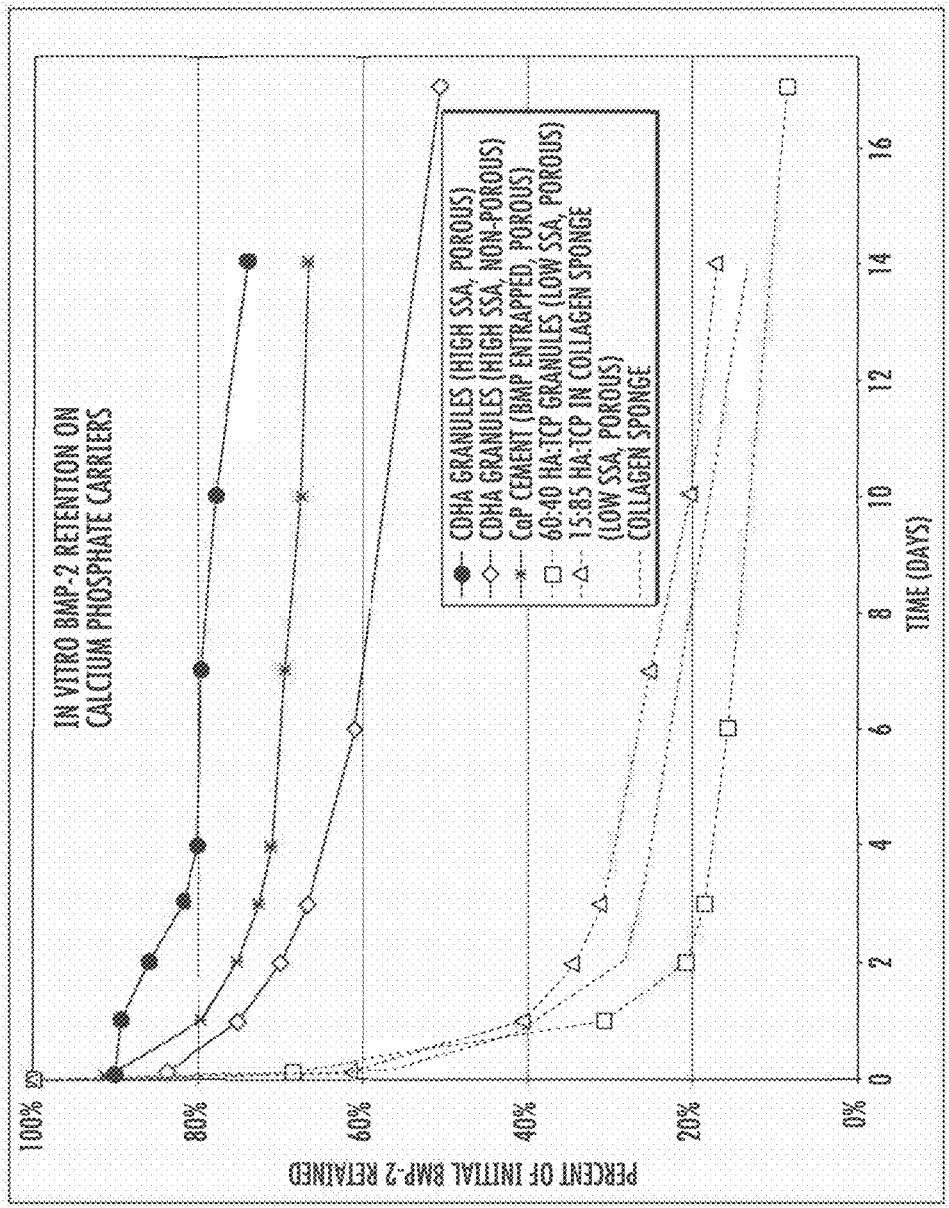
FIG. 4 shows the in vitro retention profile (% of initial) for BMP-2 delivered in CDHA porous high SSA (specific surface area) granules, CDHA non-porous high SSA granules, macroporous calcium phosphate cement (CaP), 60:40 HA/TCP porous granules, 15:85 HA/TCP porous granules compared to an absorbable collagen sponge (ACS) as a function of time in days. BMP was loaded onto the carriers in BMP buffer solution for 1 hour. The BMP-loaded granules were then incubated in a solution containing 20% bovine serum to mimic exposure to serum proteins in vivo. High specific surface area CDHA granules with and without porosity and CaP cements had superior BMP in vitro retention compared to ACS and low SSA granules either alone or contained within a collagen sponge.
Figure 5A:
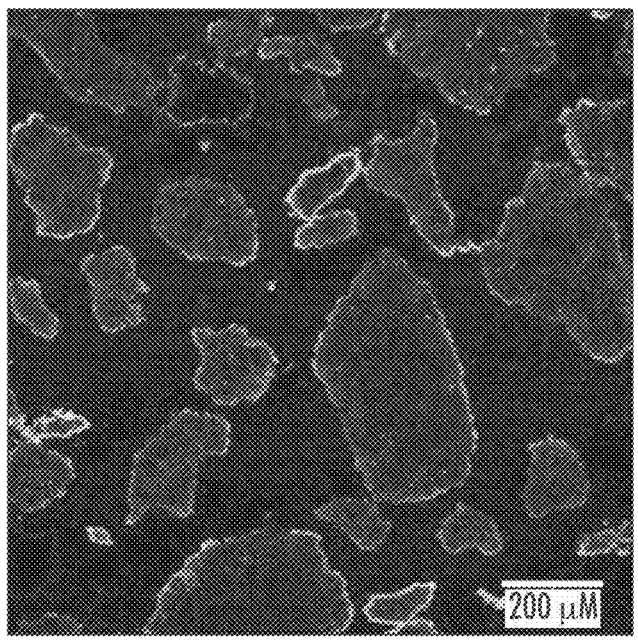
FIG. 5A-B shows photomicrographs of granules loaded with BMP-based osteoinductive proteins without (5A) and with (5B) loading buffers according to certain embodiments of the invention. 5A shows that when fluorescently labeled BMP is delivered in a weakly buffered solution, the protein is restricted to the surface of the ceramic granules. In contrast, when fluorescently labeled BMP is delivered in a well-buffered, low pH solution, the protein is able to penetrate and localize to the interior surfaces of the ceramic granules.
Figure 5B:
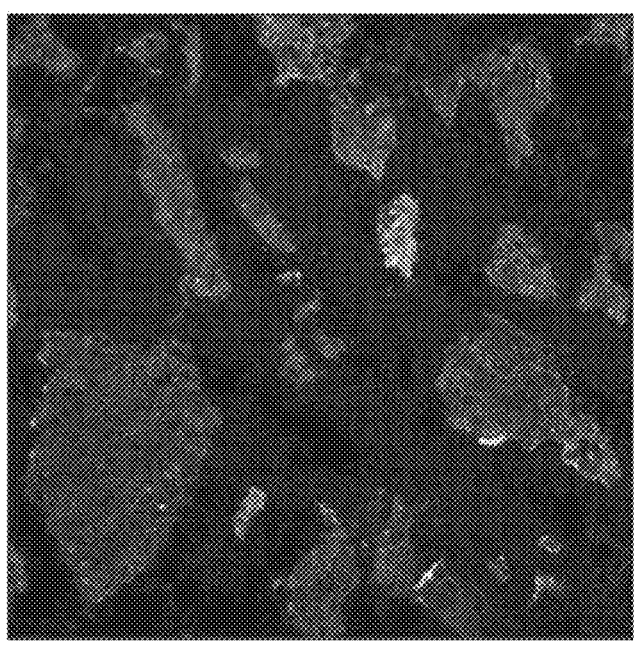

Synthetic bone grafts (also referred to interchangeably as "implants" or "constructs") utilizing the compositions of the invention generally include three components: an osteoconductive material, such as a calcium ceramic or other solid mineral body, an osteoinductive material such as a bone morphogenetic protein, and a biocompatible matrix such as a collagen sponge. As used herein, osteoconductive materials refer to any material which facilitates the ingrowth or ongrowth of osteoblastic cells including osteoblasts, pre-osteoblasts, osteoprogenitor cells, mesenchymal stem cells and other cells which are capable of differentiating into or otherwise promoting the development of cells that synthesize and/or maintain skeletal tissue. In preferred embodiments of the present invention, the osteoconductive material is a granule comprising an osteoconductive calcium phosphate ceramic that is adapted to provide sustained release of an osteoinductive substance that is loaded onto the granule. In some cases, the granule includes interconnected, complex porous structures. Exemplary granules, which the inventors have found exhibit BMP binding and elution characteristics that are optimized for use in constructs, systems and methods of the present invention are described in U.S. Provisional Patent Application No. 62/097,393 by Vanderploeg et al., the entire disclosure of which is incorporated herein for all purposes.

The granules are generally made of any suitable osteoconductive material having a composition and architecture appropriate to allow an implant of the invention to remain in place and to release osteoinductive material over time intervals optimal for the formation and healing of bone (e.g. weeks or months). While these characteristics may vary between applications, the granules generally include, without limitation, monocalcium phosphate monohydrate, dicalcium phosphate, dicalcium phosphate dehydrate, octocalcium phosphate, precipitated hydroxyapatite, precipitated amorphous calcium phosphate, monocalcium phosphate, alpha-tricalcium phosphate (α-TCP), beta-tricalcium phosphate (β-TCP), sintered hydroxyapatite, oxyapatite, tetracalcium phosphate, hydroxyapatite, calcium-deficient hydroxyapatite, and combinations thereof.

Osteoinductive materials generally include peptide and non-peptide growth factors that stimulate the generation of osteoblasts from populations of pre-cursor cells. In some embodiments, the osteoinductive material is a member of the transforming growth factor beta (TGF-β) superfamily such as BMP-2, BMP-3, BMP-4, BMP-5, BMP-6, BMP-7, BMP-9, or a designer BMP such as the BMP-GER or BMP-GER-NR chimeric BMPs described in U.S. Pre-grant application publication no. US 20120046227 A1 by Berasi et al. entitled "Designer Osteoinductive proteins," the entire disclosure of which is hereby incorporated by reference for all purposes. In other embodiments, the osteoinductive material is a fibroblast growth factor, insulin-like growth factor, platelet-derived growth factor, a small molecule, a nucleotide, a lipid, or a combination of one or more of the factors listed herein.

The third component of implants (also referred to herein as "constructs") according to the present invention is the biocompatible matrix, which can be any suitable biocompatible material which (a) when used in concert with the granules, exhibits sufficient rigidity and/or column strength to withstand the loads placed upon it when implanted, (b) which does not cause excessive inflammation (i.e. inflammation sufficient to inhibit or prevent the formation of new bone or the healing of a broken bone), inhibit the proliferation of osteoblasts, or otherwise interfere with the activity of the granules and/or the osteoinductive material, and (c) has sufficient cohesion over an appropriate interval to permit the deposition of new bone within a defined area. In addition, the biocompatible matrix is optionally degradable and/or osteoconductive. The biocompatible matrix is, in various embodiments, hyaluronic acid (HA), and functionalized or modified versions thereof, collagen, whether animal or recombinant human, gelatin (animal or recombinant human), fibrin, chitosan, alginate, agarose, self-assembling peptides, whole blood, platelet-rich plasma, bone marrow aspirate, polyethylene glycol (PEG) and derivatives thereof, functionalized or otherwise cross-linkable synthetic biocompatible polymers including poly(lactide-co-glycolide), poly (caprolactone), poly(lactic acid), poly(glycolic acid), poloxamers and other thermosensitive or reverse-thermosensitive polymers known in the art, and copolymers or admixtures of any one or more of the foregoing.

Technical Considerations for Implant Design

Implants of the invention, which include the osteoinductive materials, granules and biocompatible matrices as described above, generally have characteristics which are tailored to the facilitation of bone growth and healing and which are not exhibited by currently available synthetic bone grafting materials. The relevant characteristics of implants according to the present invention include at least (a) kinetics of release of osteoinductive materials that are appropriate for the application, (b) residence time appropriate to facilitate but not interfere with new bone formation, (c) macroporosity that permits the infiltration of cells and tissues, including new vascular tissue that accompanies the formation of new bone, and (d) sufficient rigidity/or and compression resistance to withstand loads applied to the implant.

BMPs induce bone formation primarily by stimulating differentiation of osteoblast progenitors either resident at the site of repair in the bone envelope or in the surrounding soft tissue envelope. Physiological bone repairs are stimulated by the release of picogram/femtogram amounts of BMPs stored in the mineral phase of bone and from newly synthesized BMPs secreted by bone progenitor cells at the site of the repair. These two sources of BMP maintain BMP concentrations at the site of repair at physiological levels for the appropriate amount of time to induce a successful bone repair.

Exogenous BMPs are, ideally, delivered in constructs which elute BMP in amounts and over intervals that mimic the physiological BMP response. It should be noted, however, that the administration of much larger pharmacological BMP concentrations is generally required to achieve physiological concentrations of BMPs at the cellular level and to maintain the physiological concentrations for the appropriate amount of time. This is due to a combination of factors that are not totally understood. Without wishing to be bound by any theory, one factor driving the need for super-physiological BMP concentrations in these constructs may be the inability of exogenous BMP to mimic the efficiency of physiological local release of endogenous BMPs from bone and newly formed endogenous BMPs from cells. In addition, rhBMPs are generally insoluble at physiological pH, so (again, not wishing to be bound by any theory) much of the exogenously delivered BMP may not be physiologically available.

The amount of exogenous rhBMP required to stimulate bone repair appears to be species dependent. Empirical data suggests that lower concentrations of exogenous rhBMPs are required to stimulate bone formation in small animals such as rodents and rabbits compared to larger animals including dogs, sheep and goats. Nonhuman primates and humans appear to require the highest concentrations of exogenous rhBMPs to stimulate bone repair. For example, the FDA approved concentration of rhBMP-2 delivered in an absorbable collagen sponge (ACS) for bone repair in dogs is 0.2 mg/mL compared to 1.5 mg/mL in people. Again, the factors contributing to this difference in required exogenous rhBMP concentration are not clearly understood, but those of skill in the art will understand that inter-species differences must be considered in evaluating findings in animal models for its applicability to human patients.

Similarly, the interval over which BMPs must be delivered to tissues varies among species: BMP residence time for repairs in rodents and rabbits can be as short as several days due to their rapid intrinsic rate of bone formation, while nonhuman primates and human patients generally requires several weeks BMP residence time. While not wishing to be bound by any theory, the longer interval observed in primates and humans appears to be related to the amount of time for the healing process to transition from an initial catabolic inflammatory phase caused by the surgery or trauma to an anabolic phase involving the migration and differentiation of osteoblast progenitors and associated new blood vessel units to support the fusion/repair process. Short BMP residence time optimal for rodents may not maintain physiological BMPs levels for a sufficient amount of time to stimulate bone repair in animals with slower bone formation rates. Conversely, BMP may not be released in sufficient amounts from a carrier with a longer retention profile to stimulate bone formation in animals with rapid intrinsic bone formation rates.

As one example, the residence time of BMPs delivered locally in buffer solution to a repair site is extremely short, and even when relatively large amounts of BMP are delivered in solution, an adequate bone response is only stimulated in rodent models. For applications in non-human primates and human patients, an extended-release carrier is preferably used to localize BMP to sites of treatment for a period of weeks.

One strategy for providing extended local BMP release is to utilize carriers that mimic the binding of BMP to endogenous extracellular matrix. As one example, collagenous carriers exhibit longer BMP residence times than BMP solutions, due (without being bound to any theory) to the intrinsic binding properties of BMP to extracellular matrix components including endogenous collagen. Ceramic carriers including calcium phosphate matrices (CPM) more closely mimic physiologic release of BMP from bone with very long residence times. The release of BMP from ceramic carriers may require the same osteoclastic resorption observed in release of BMP from bone. Based on this unique property, implants comprising ceramic components embedded within composite carriers, as are used in the present invention, may be superior vehicles for BMP delivery compared to other naturally occurring and synthetic biomaterials.

In addition to optimizing bone response temporally, the ideal carrier provides optimal spatial bone response. One effect seen in some delivery systems is the release of BMP into hematoma/seroma fluid around the site of implantation, contributing to heterotopic or ectopic bone formation. BMP-2 is registered for use in people delivered in an absorbable collagen sponge (ACS) placed in an interbody cage for lumbar interbody spine fusions and with the ACS sponge alone for open tibia fracture repair. Although ACS meets many of the requirements for a carrier, release of BMP from ACS is rapid particularly in the first 24 hours. The consequences of rapid BMP release are associated to some degree with the observations of ectopic/heterotopic bone, post-operative soft tissue swelling/transient fluid formation, and transient bone resorption observed with the use of INFUSE®.

Again, without wishing to be bound by any theory, the rapid release of BMP from the ACS sponge is believed to be due primarily to serum proteins having a higher affinity for BMP than collagen. The affinity of BMP for collagen allows for efficient loading of BMP and transfer of the BMP/carrier to the surgical repair. However once in contact with serum proteins present within the repair associated with surgical bleeding, BMP rapidly releases from the sponge and is trapped within the hematoma at the repair site. Conversion of the hematoma to a seroma during the first week following repair, as part of the healing process, allows released BMP to migrate with the seroma fluid into available tissue planes, contributing to heterotopic or ectopic bone formation.

With respect to the avoidance of trabecular bone resorption, the rapid release of BMP following administration of BMP/ACS within metaphyseal bone or into the trabecular bone associated with interbody fusions where the endplates are penetrated results in rapid upregulation of osteoblast precursor cells in a location where there are also significant numbers of osteoclast precursor cells. As a result of normal cross talk between these two cell types, sufficient mature osteoclasts are generated to cause transient resorption of trabecular bone prior to bone formation. This phenomenon is partially responsible for osteolysis sometimes observed in interbody fusions and metaphyseal bone repairs associated with the use of INFUSE®.

Structural Considerations

In order to provide temporally and spatially optimal delivery of BMPs, carriers according to the various embodiments of the present invention are preferably macroporous such that they allow penetration of new blood vessels and bone forming cells into the repair site to generate a uniform full thickness repair (FIG. 1). Carriers that aren't macroporous often result in repairs that have mechanically inferior shells of bone on their surface that do not fully penetrate into the repair. The absorbable collagen sponge (ACS) used to deliver BMP-2 in INFUSE® has a void volume in excess of 90%. However the average pore size of ACS is relatively small. Individual cells such as macrophages and monocytes can penetrate into the sponge to initiate resorption of the carrier and release of the bound BMP. BMP can also freely diffuse out of the sponge. However the pore size isn't large enough to allow penetration of blood vessel units required to initiate bone formation. As a result, bone formation in response to treatment with BMP-2/ACS generally occurs in the highly vascular granulation tissue outside the resorbing collagen sponge rather than inside the sponge. Rapid mineralization of newly forming bone at the periphery of the resorbing ACS can lead to less than optimal hallow callus architecture, as illustrated in FIG. 1A-B. In contrast granulated calcium phosphate matrix or carriers with macroporosity in excess of 300 um allow for rapid penetration of BMP induced blood vessels within the carrier leading to more uniform, mechanically superior, guided tissue repair callus constructs.

Optimal BMP carriers should also preferably be sufficiently compression resistant to ensure a space for new bone formation without interference from surrounding soft tissues. This is particularly important for segmental defects and posterolateral spine fusion where soft tissues can protrude into the repair site. The absorbable collagen sponge (ACS) used to deliver BMP-2 in INFUSE does not provide sufficient compression resistance to prevent the overlying soft tissues from limiting the size of the posterolateral fusion mass. While some products, such as AMPLIFY® developed by Medtronic, Minneapolis, Minn., deliver BMP using a compression resistant collagen matrix (CRM) composed of collagen impregnated with HA/TCP granules for use in posterolateral spine fusions, no such product has been approved for use in humans at this time. Nonetheless, the addition of calcium phosphate granules may confer sufficient compression resistance to the AMPLIFY® product to demonstrate efficacy in posterolateral fusions in people. However the lack of macroporosity within the collagen and the less than optimal BMP binding characteristics of the CRM carrier necessitated higher BMP concentrations.

Solutions and Kits for Protein Loading of Granules

In constructs of the present invention, BMPs are primarily carried by the ceramic granules embedded within the construct. In general, using current methods, BMP accumulates on the exterior surfaces of the granules, creating a protein "rim" rather than penetrating the highly porous structures of the granules that are preferably used in the various embodiments of the invention. The protein rim may contribute to burst release of BMP following construct implantation, while penetration of BMP into the granules may contribute to an extended release profile insofar as BMP associated with internal surfaces of the granules are shielded from release until the implanted granules degrade, for example due to osteoclastic activity at the site of implantation. Without wishing to be bound by any theory, it is believed that, in general, BMPs are highly soluble in low pH, low-ionic strength buffers; state of the art BMP buffers with these characteristics generally have low buffering capacities. On the other hand, granules used in constructs of the present invention are generally alkaline; this difference may contribute to the relatively limited infiltration of BMP into granules using current methods.

The inventors have discovered two factors that facilitate the penetration of BMP into the interior pore structure of the granules: first, the inventors have found that pre-treatment of the granules with an acid solution (for example, 50 mM hydrochloric acid (HCl) or, more preferably, 500 mM acetic acid), also referred to as "etching" the granules, prior to incubation of the granules with BMP-containing solutions (referred to as the "protein loading" step) aids in the transport of BMP into the interior pore structure of the granules. Second, the inventors have found that certain compositions, including generally those with relatively higher buffering capacity buffer, also facilitate transport of BMP into the interior pores of the granules. Each of these factors is discussed in turn below:

With respect to etching of granules prior to protein loading, the inventors have found that pre-treatment of the granules by 15 minute-4 hour incubation in an acidic solution, preferably 500 mM acetic acid, at a ratio of 10 mL per gram weight of calcium-deficient hydroxyapatite (CDHA) granules improves infiltration of the BMP into the granules. Treating granules with acid lowers the pH of the granules to pH 5.5-6.0. Etching can also result, in certain cases when the buffer is of sufficiently high buffer capacity and sufficiently low pH, in increased release of BMP into solution, e.g. during washing of the granules. The skilled artisan will appreciate, additionally, that protein loading and elution results similar to those obtained by etching of granules may be obtained in some instances by utilizing granules having an inherently low (e.g. less than 7.0) pH in their as-manufactured state.

With respect to new BMP buffers, the inventors have found that several buffer components and/or compositions can result in improved infiltration of BMPs into the internal pores of granules. A non-limiting listing of buffers according to the present invention (as well as the clinically used rhBMP-2 buffers for purposes of comparison) appears in Table 1:

TABLE 1

EXEMPLARY BUFFER COMPOSITIONS

| Buffer | Composition | pH |
|---|---|---|
| 1x dBMP Buffer | 5 mM Glutamic Acid<br>0.15% Glycine<br>1% Sucrose<br>0.01% Polysorbate-80<br>Water for Injection | 4 |
| 5x dBMP Buffer | 25 mM Glutamic Acid<br>0.75% Glycine<br>1% Sucrose<br>0.01% Polysorbate-80<br>Water for Injection | 3.5 |
| 10x dBMP Buffer | 50 mM Glutamic Acid<br>1.5% Glycine<br>1% Sucrose<br>0.01% Polysorbate 80<br>Water for Injection<br>pH Adjusted with HCl | 3 |
| BMP2 buffer-1 | 5 mM Glutamic Acid<br>2.5% Glycine<br>0.5% Sucrose<br>5 mM NaCl<br>0.01% Polysorbate 80<br>Water for Injection | 4.5 |
| BMP2 buffer-2 | 25 mM Glutamic Acid<br>2.5% Glycine<br>0.5% Sucrose<br>2 mM NaCl<br>0.01% Polysorbate 80<br>Water for Injection | 4.5 |
| BMP12 buffer | 25 mM Glutamic Acid<br>2% Glycine<br>1% Sucrose<br>0.01% Polysorbate 80<br>Water for Injection | 4 |

The inventors have found that the "5x" and "10x" buffer formulations improve BMP infiltration into granules relative to the BMP-2 buffers used previously. More generally, and without wishing to be bound by any theory, weakly acidic buffer solutions with buffering capacities sufficient to maintain low pH (e.g. less than 5.0) when incubated with granules are preferred in various embodiments of the present invention. Specifically, while the solutions set forth in Table 1 are buffered by glutamic acid and/or glycine, a variety of other buffering agents are useful in protein loading solutions of the present invention, including lactic acid, acetic acid, formic acid, malic acid, malonic acid, aspartic acid, citric acid, tartaric acid, phosphoric acid, fumaric acid and/or succinic acid. In preferred cases, the buffering agent has a pKa between about 2.3 and 4.5, while the buffer as a whole preferably has a pH between 3.5 and 4.0.

In addition to buffering agents, solutions of the present invention can incorporate one or more additives, including without limitation 0.01%-0.1% (w/v) polysorbate-80, 0.5%-5% (w/v) Sucrose, 0.5%-5% (w/v) Trehalose, 0.5%-5% (w/v) Sorbitol or 0.5%-5% (w/v) Mannitol.

By way of example (and not limitation), one buffer solution according to the present invention has a composition of (i.e. consists essentially of) 5 mM Glutamic acid, 0.15% (w/v) Glycine, 1% Sucrose, and water with a pH of 4.0. Another buffer solution is 50 mM Glutamic acid, 1.5% (w/v) Glycine, 1% Sucrose, and water with a pH adjusted to 3.0 with hydrochloric acid, and another suitable buffer is 50 mM Glutamic acid, 0.75% (w/v) Glycine, 1% Sucrose, and water with a pH of 3.5. Yet another buffer solution is 25 mM Glutamic acid, 0.75% (w/v) Glycine, 1% Sucrose, and water with a pH adjusted to 3.5 with HCl, another is 25 mM Glutamic acid, 0.75% (w/v) Glycine, 1% Sucrose, and water with a pH of 3.7, and another buffer solution is 25 mM Glutamic acid, 2% (w/v) Glycine, 1% Sucrose, and water with a pH of 4.0. Still another suitable buffer solution is 50 mM Glutamic acid, 1.5% (w/v) Glycine, 1% Sucrose, and water with a pH of 3.7.

FIG. 6 includes several fluorescent micrographs of naïve (panels A, B, C) and etched (panels E, F, G) granules treated with buffers having various pH and buffering capacities during the protein loading step. In naïve granules, a protein rim was visible in all conditions, and in both naïve and etched granules, infiltration of the granules improved as the buffering capacity and acidity of the buffer solution increased. Importantly, infiltration of BMP into granules was improved by etching when intermediate buffering capacity buffers were used (panels B and E), but good infiltration was also observed in naïve granules loaded in buffers with high-buffering capacity. These results indicate that it is not strictly necessary to pair high-buffering capacity, low pH protein loading buffers with granule etching to achieve good BMP infiltration into the granules; accordingly, various embodiments of the present invention utilize etching and/or the improved protein loading buffer.

Figure 7A:
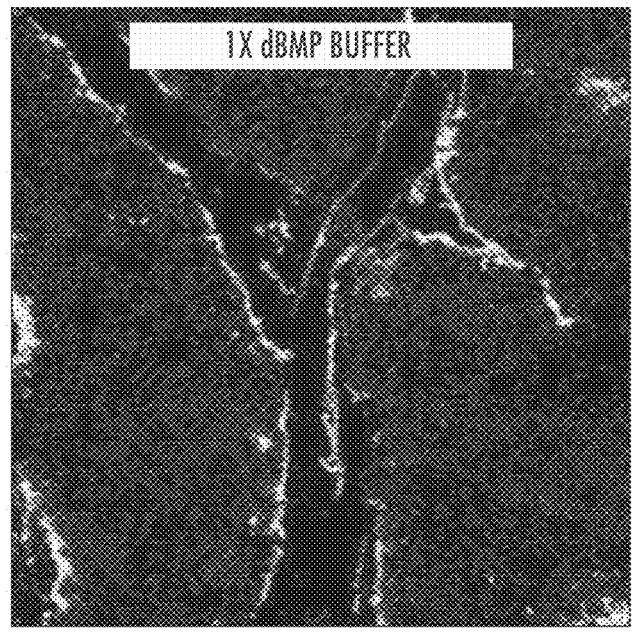
FIG. 7A-B shows fluorescent micrographs of BMP-loaded granules and FIG. 7C-D shows quantification of the signal from fluorescently labeled BMP protein throughout the granules when delivered in a weak buffer (1× dBMP Buffer) or a strong buffer (1M Acetic Acid).
Figure 7B:
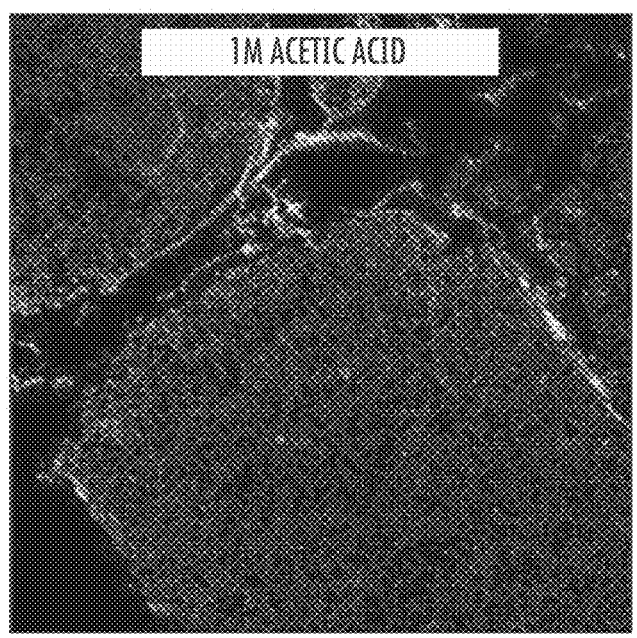
Figure 7C:
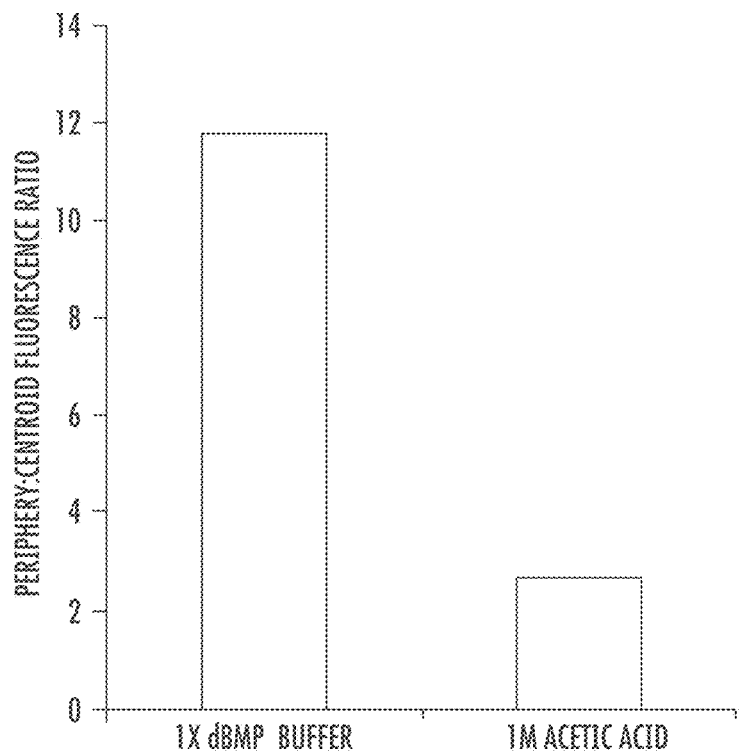
Figure 7D:
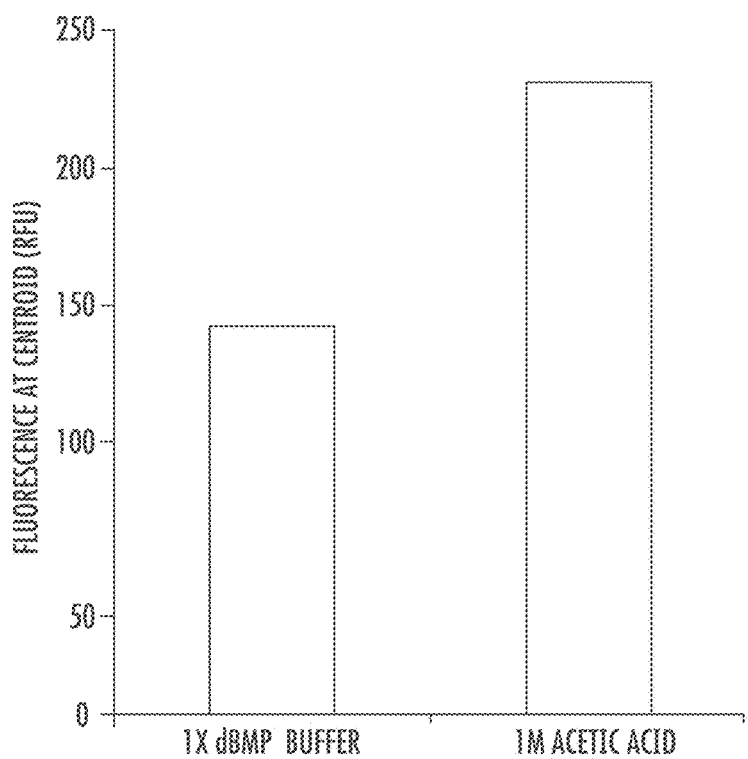
Figure 8:
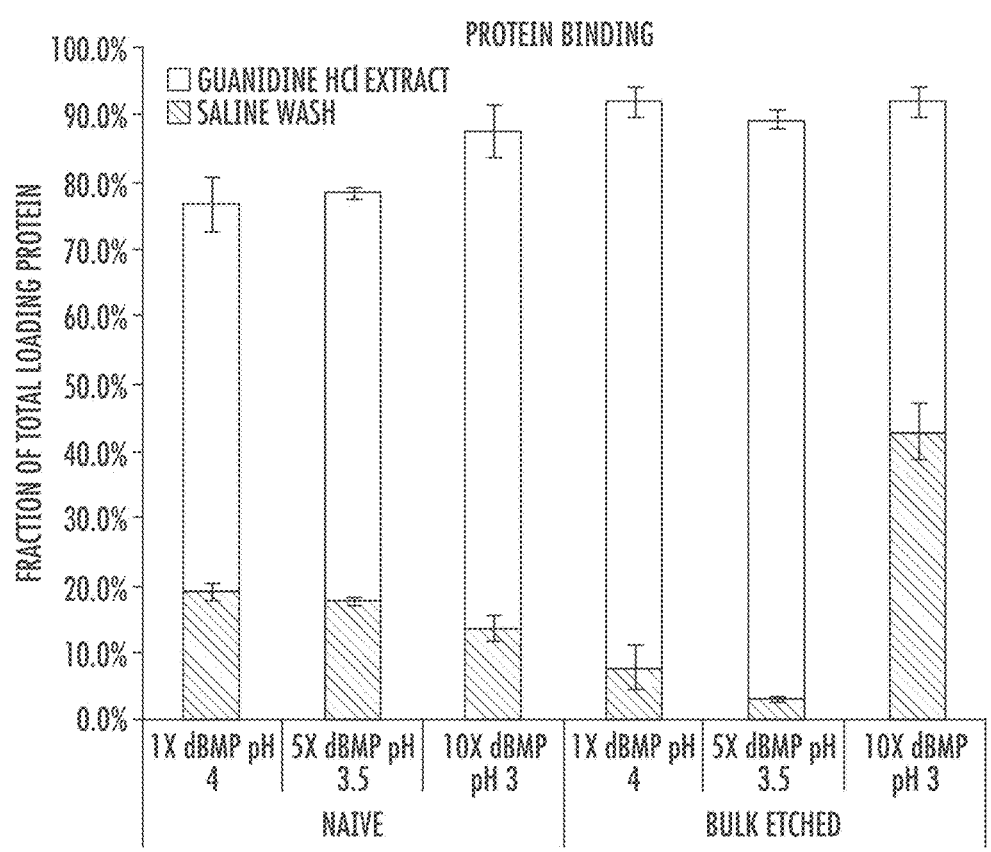
FIG. 8 illustrates the partitioning of the protein between a saline wash and a guanidine HCl extract following incubation of BMP with untreated or etched granules in varying buffer compositions. The protein in the saline wash is considered loosely bound to the granules, whereas the protein in the guanidine HCl extract is considered tightly bound to the granules. In untreated granules, the amount of loosely bound BMP decreases as the buffering capacity increases and the pH decreases (i.e., from "1× dBMP" to the "10× dBMP" buffer conditions). For etched granules a similar pattern was observed until the BMP was loaded in the high buffering capacity pH 3 buffer (10× dBMP) in which case the fraction of loosely bound protein increased dramatically over that for the 1× dBMP and 5× dBMP conditions.
Figure 9:
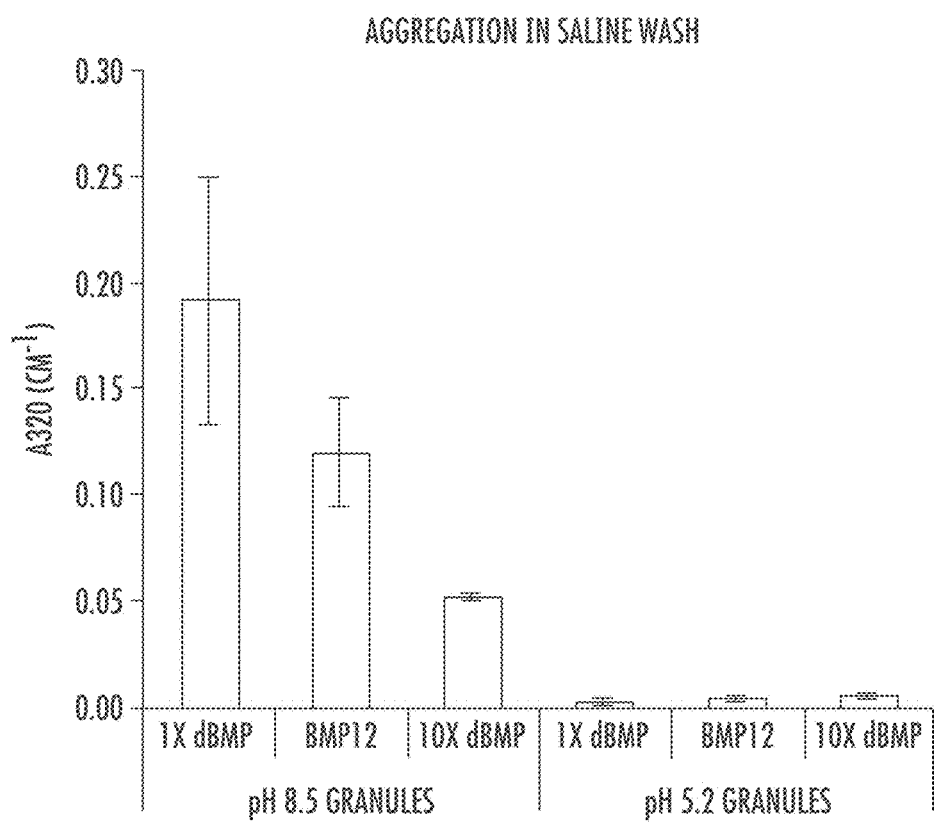
FIG. 9 shows that in alkaline granules (e.g. pH 8.5) the BMP tends to be aggregated (high A320 values) and the extent of aggregation generally decreases as the strength of the buffer increases (1×→5×→10× dBMP Buffers). Additionally, in low pH granules (e.g. pH 5.2) the BMP tends to be less aggregated overall, thereby better enabling delivery to the interior of the granules.

The inventors have also found, however, that different combinations of etching and buffering can result different degrees of apparent binding between the granule and BMP, as evidenced by the fraction of BMP eluted in a saline wash of the BMP loaded granules. FIG. 7 illustrates the BMP fractions eluted in the saline wash (dark bars) and a subsequent guanidinium chloride protein extraction (light bars). In general, about 20% or less of the BMP elutes during the saline wash, though in etched granules loaded with 10×BMP buffer almost 40% of the BMP eluted during the wash, while etched granules loaded with 5×BMP buffer released less than 10% of their BMP during the wash. Without wishing to be bound by any theory, it is believed that these differences may correlate with differences in BMP release by implanted constructs, and the present invention encompasses constructs with BMP release kinetics that can be tuned by varying the BMP loading buffer and/or the etching of the granules.

In use, protein-loaded granules generated through the use of the compositions and methods of the present invention form one part of a multipart construct for use in treating patients. As is described above, these constructs generally include an osteoinductive protein that is preferably associated with and elutes from granules with complex and interconnected networks of micropores of varying size, which granules are in turn embedded, inserted, or otherwise in contact with a polymer matrix that has a macroporous structure to facilitate cellular and vascular infiltration, and which is characterized by a residence time on the order of several weeks (advantageously permitting extended delivery of osteoinductive protein as more specifically described above) and a stiffness and compression resistance sufficient to enable the construct to remain intact and provide structural support for new bone growth when implanted. These constructs will typically include a porous polymer matrix preferably comprising collagen but, optionally comprising other naturally-occurring or synthetic polymers.

Next Generation Carriers

In yet another aspect, the present invention relates to three-part constructs that satisfy the design criteria discussed above. Table 1 sets forth exemplary, rather than comprehensive, constructs according to various embodiments of the present invention. It will be appreciated that other constructs which meet the design criteria above are within the scope of the present invention.

TABLE 2

EXEMPLARY CONSTRUCS

| | Design A | Design B |
|---|---|---|
| Biocompatible Matrix | Fibrillar and soluble collagen sponge | Poly-lactide-co-caprolactone polymer (PLCL) |
| Granule Size & Geometry | 425-800 µm Angular | 100-425 µm Angular |
| Granule pH | 5.5-6.0 | 5.5-6.0 |
| Granule Density | 0.24 g/cc | 0.225 g/cc |
| Collagen Coating | None | None |
| Embedded Mesh | None | None |
| Matrix Dimensions | 100 × 24 × 4 mm | 100 × 24 × 4 mm |

The constructs in Table 2 include BMP-loaded granules embedded within a macroporous biocompatible matrix. The rigidity of the constructs is increased, in some instances, by the inclusion of one or more stiffening elements, such as one or more rods, fibers, or a mesh or braided framework. With or without the inclusion of such stiffening elements, constructs according to the various embodiments of the present invention are generally rigid enough to withstand the forces applied to the construct during and after implantation.

The constructs described in Table 2 can be formed using methods already known in the art. For example, U.S. Pat. No. 9,163,212 to McKay (which is incorporated by reference herein for all purposes) describes a process of forming a "cell delivery matrix" by molding, which generally begins with a slurry comprising a polymer matrix material such as collagen and ceramic particles in a liquid solvent, which can be water or an aqueous solution (e.g. physiological saline, dextran or sucrose solution, etc.), or a polar protic solvent such as glycerol or a glycerol ester. The liquid solvent can constitute about 5 to 70% by weight of the mixed slurry. The slurry is then placed in a mold and, optionally compressed, heated, lyophilized and/or cross-linked. With respect to cross-linking, Constructs of the present invention can be bundled into kits that can include one or more of a BMP loading solution, an applicator for applying the loading solution to the construct and/or for placing the construct in the body of a patient, and instructional materials which describe use of the kit, or its components, to perform the methods of the invention. Although exemplary kits are described herein, the contents of other useful kits will be apparent to the skilled artisan in light of the present disclosure. Each of these kits is included within the invention.

The invention includes a kit for treatment to prevent loss of and/or increase bone mass in a patient in need thereof. The kit includes construct as described above, along with an osteogenic protein, which can be in lyophilized or other dry form or in solution. If the protein is lyophilized or otherwise not in solution, the kit may also include a diluent or loading buffer along the lines described above. The kit also includes an applicator, including, but not limited to, a syringe for adding fluid to the protein vessel and/or wetting the construct, or a delivery apparatus for placing the construct, loaded with the osteoinductive protein, into the body of a patient. Further, the kit can optionally include an instructional material setting forth the pertinent information for the use of the kit to treat or prevent bone loss, promote union or knitting of a fracture, and/or otherwise increase bone mass or treat a bone condition in the patient.

CONCLUSION

Throughout this application, reference is made to "macropores," "micropores" and macro- and microporosity. In general, macropores have a cross-sectional dimension greater than 100 microns, while micropores are between 100 nm and 100 microns. Pores less than 100 nm are referred to as nanopores.

Except when noted, the terms "patient" or "subject" are used interchangeably and refer to mammals such as human patients and non-human primates, as well as veterinary subjects such as rabbits, rats, and mice, and other animals. Preferably, patient refers to a human.

"Effective amount", or "therapeutically effective amount," as the terms are used interchangeably herein, is an amount that when administered to a tissue or a mammal, preferably a human, mediates a detectable therapeutic response compared to the response detected in the absence of the compound. A therapeutic response, such as, but not limited to, inhibition of and/or decreased fibrosis, increased bone mass or bone density, and the like, can be readily assessed by a plethora of art-recognized methods, including, e.g., such methods as disclosed herein.

As used herein, to "treat" means to prevent or reduce the frequency or severity of the symptoms of a disease or condition (e.g., decreased bone density, fracture, fibrosis, and the like) affecting a patient. The term includes the application, administration or use of the compositions, systems, and methods described herein to prevent or delay the onset of the symptoms, complications, or biochemical indicia of a disease, alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

"Instructional material," as that term is used herein, includes a publication, a recording, a diagram, or any other medium of expression which can be used to communicate the usefulness of the system, apparatus, composition, or combination thereof for affecting, alleviating or treating various diseases, disorders or conditions. Optionally, or alternately, the instructional material can describe one or more methods of alleviating the diseases or disorders in a cell, a tissue, a mammal, etc. The instructional material of the kit may, for example, be affixed to a container that contains a system, apparatus and/or composition of the invention or be shipped together with a container which contains the system, apparatus and/or composition. Alternatively, the instructional material may be shipped separately from the container with the intention that the recipient uses the instructional material and the compound cooperatively.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A composition, comprising: a porous biocompatible polymer matrix having a plurality of macropores having an average size of about 100 μm to about 500 μm; admixed with a calcium ceramic granule having an average diameter of about 425 μm to about 800 μm and having an interconnected network of micropores defining at least one surface on an interior of the granule and wherein the calcium ceramic granule has a pH of less than 7, as measured in a slurry of said granules and water or another neutral, non-buffering solution.

2. The composition of claim 1, further comprising an osteoinductive protein associated with the at least one interior surface, wherein a concentration of the osteoinductive protein near the centroid of the calcium ceramic granule is not less than about 33% of a concentration of the osteoinductive protein on the external surface of the calcium ceramic granules.

3. The composition of claim 1 wherein the porous biocompatible matrix additionally has a plurality of macropores with an average diameter of about 1 mm to 2 mm.

4. The composition of claim 1 where the porous biocompatible matrix is comprised of collagen.

5. The composition of claim 1 wherein the porous biocompatible matrix is comprised of a synthetic polymer.

6. The composition of claim 1, wherein the composition has sufficient column strength to resist at least 50 kPa of pressure at 50% linear strain.

7. The composition of claim 2, wherein said calcium ceramic granule retains at least 50% of the osteoinductive protein for a period of at least 7 days after implantation.

8. A method of treating a patient, comprising the steps of:
contacting a bony tissue of the patient with a composition, comprising:
a porous biocompatible matrix, the matrix including a plurality of macropores having an average size of about 100 μm to about 500 μm;
a calcium ceramic granule contacting the porous biocompatible matrix, said granule having an interconnected network of micropores defining at least one surface on an interior of the granule, wherein said granule has an average diameter of about 425 μm to about 800 μm and a pH of less than 7, as measured in a slurry of said granules and water or another neutral, non-buffering solution; and
an osteoinductive protein associated with the at least one surface on the interior of the granule, wherein the osteoinductive protein is distributed on a portion of the at least one surface near the centroid of the granule and on a portion of the at least one surface near the exterior of the granule.

9. The method of claim 8, wherein the bony tissue is selected from the group consisting of a site of a traumatic injury to the bone and a vertebra.

10. The composition of claim 8, wherein the calcium ceramic granule has a pH of 5.5 to 6.0.

11. The method of claim 8, wherein the porous biocompatible matrix comprises collagen.

12. The method of claim 8, wherein the porous biocompatible matrix comprises a synthetic polymer.

13. The method of claim 8, wherein a concentration of the osteoinductive protein near the centroid of the calcium ceramic granule is not less than about 33% of a concentration of the osteoinductive protein on the external surface of the calcium ceramic granules.

14. The method of claim 8, further comprising the step of wetting the composition with a solution comprising the osteoinductive protein, thereby associating the osteoinductive protein with the at least one surface.

15. A kit for treating a patient, comprising:
a carrier, comprising:
a porous biocompatible matrix, the matrix including a plurality of macropores having an average size of about 100 μm to about 500 μm; and
a calcium ceramic granule contacting the porous biocompatible matrix, said granule having an interconnected network of micropores defining at least one surface on an interior of the granule, wherein said granule has an average diameter of about 425 μm to about 800 μm and a pH of less than 7, as measured in a slurry of said granules and water or another neutral, non-buffering solution; and
a vessel holding an osteoinductive protein in a form in which the osteoinductive solution can be added to a fluid to form a solution, the solution being adapted to wet the carrier, thereby associating the osteoinductive protein with the at least one surface on the interior of the granule, thereby forming an implant.

16. The kit of claim 15, wherein the porous biocompatible matrix additionally has a plurality of macropores with an average diameter of about 1 mm to 2 mm.

17. The kit of claim 15, wherein the porous biocompatible matrix is comprised of collagen.

18. The kit of claim 15, wherein the porous biocompatible matrix is comprised of a synthetic polymer.

19. The kit of claim 15, wherein the implant has sufficient column strength to resist at least 50 kPa of pressure at 50% linear strain.

\* \* \* \* \*